United States Patent
Liu et al.

(10) Patent No.: US 7,022,527 B2
(45) Date of Patent: Apr. 4, 2006

(54) METHOD FOR THE SIMULTANEOUS AND DIRECT DETERMINATION OF SERUM CHOLESTEROL IN HIGH AND LOW DENSITY LIPOPROTEINS USING INFRARED SPECTROSCOPY

(75) Inventors: Kan-Zhi Liu, Manitoba (CA); Anthony Shaw, Manitoba (CA); Henry H. Mantsch, Berlin (DE)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/485,413

(22) PCT Filed: Sep. 11, 2002

(86) PCT No.: PCT/CA02/01377

§ 371 (c)(1),
(2), (4) Date: Aug. 2, 2004

(87) PCT Pub. No.: WO03/023397

PCT Pub. Date: Mar. 20, 2003

(65) Prior Publication Data

US 2004/0248309 A1    Dec. 9, 2004

Related U.S. Application Data

(60) Provisional application No. 60/327,766, filed on Oct. 10, 2001.

(30) Foreign Application Priority Data

Sep. 12, 2001  (CA) .................................... 2357338

(51) Int. Cl.
*G01N 33/92* (2006.01)

(52) U.S. Cl. ........................ 436/71; 436/164; 436/171; 356/51

(58) Field of Classification Search ................... 436/63, 436/71, 164, 171; 356/51
See application file for complete search history.

(56) References Cited

U.S. PATENT DOCUMENTS

| 5,252,488 A | 10/1993 | Purdie |
| 5,553,610 A * | 9/1996 | Lodder ........................ 600/310 |
| 6,226,082 B1 * | 5/2001 | Roe ........................... 356/301 |

FOREIGN PATENT DOCUMENTS

| EP | 0 597 268 | 5/1994 |
| WO | WO/01/07894 | 2/2001 |

OTHER PUBLICATIONS

Gotto et al. Nature, vol. 224, 1969, pp. 69-70.*
Lopez et al. Applied Spectroscopy, vol. 54, No. 12, 2000, pp. 1771-1776.*
Multianalyte Serum Assays from Mid IR Spectra of Dry Films on Glass Slides, Applied Spectroscopy, vol. 54, No. 6, Jun. 2000, pp. 885-889.
Infrared Spectroscopy in Clinical and Diagnostic Analysis, Encyclopedia of Analytical Chemistry, Edited by Robert A. Meyers, Wiley & Sons Ltd, 2000, pp. 1-20.

* cited by examiner

*Primary Examiner*—Maureen M. Wallenhorst
(74) *Attorney, Agent, or Firm*—Michael R. Williams; Adrian D Battison; Ryan W. Dupuis (57) ABSTRACT

A method of simultaneously determining the concentrations of cardiovascular risk markers selected from the group consisting of High Density Lipoprotein cholesterol (HDL-C), Low Density Lipoprotein cholesterol (LDL-C), total cholesterol, triglycerides and oxidized LDL using infra-red and/or near infrared light is described.

6 Claims, 9 Drawing Sheets

METHOD FOR THE SIMULTANEOUS AND DIRECT DETERMINATION OF SERUM CHOLESTEROL IN HIGH AND LOW DENSITY LIPOPROTEINS USING INFRARED SPECTROSCOPY

This application is a national phase application of PCT CA02/01377, filed Sep. 11, 2002 which claims the benefit of U.S. Provisional Application 60/327,766, filed Oct. 10, 2001 and Canadian Patent Application 2,357,388, filed Sep. 12, 2001.

BACKGROUND OF THE INVENTION

Cardiovascular disease remains the leading cause of death in North America and Western Europe. The majority of these deaths are due to myocardial or cerebral infarction, with atherosclerosis being the principal cause (McGill Jr., 1988, Clin Chem 34: 1333–1339). It has long been recognized that cholesterol plays a role in the formation of atherosclerotic plaques; the compound was first noted as a lesion component almost a century ago by Windaus. More recently, it has become clear that total serum cholesterol consists of subfractions that must be considered individually in order to assess the risk profile. In particular, above normal levels of cholesterol sequestered in high density lipoproteins (HDL cholesterol, or HDL-C) carries a message opposite to that implied by elevated low density lipoprotein cholesterol (LDL-C). The principal physiochemical risk factor is a high serum level of the primarily atherogenic LDL cholesterol (Schwartz et al., 1991, Clin Cardiol 14: 11–116), since these lipoproteins promote the deposition of plasma lipids in the artery wall and elicit the formation of fatty streaks and/or atherosclerotic plaques. LDL-C is now recognized as a key factor in the development of atherosclerosis. On the other hand, HDL is associated with decreased incidence of atherosclerosis. Produced mainly in the liver and intestine (it can also be derived as metabolic by-products of chylomicron and VLDL catabolism), the main function of HDL is the transport of cholesterol from the peripheral cells to the liver, i.e., "reverse cholesterol transport" (Golmset, 1968, J Lipid Res 9: 155–167).

While a wide variety of methods have been proposed for the determination of serum LDL cholesterol, including electrophoresis, HPLC, sequential and density gradient ultracentrifugation, precipitation-based methods, and immunoseparation, the standard routine laboratory test is an indirect one. The Friedewald formula has proven to be extraordinarily useful in providing a close approximation to true LDL values, particularly since no practical alternative has emerged for large scale routine testing. Despite a good correlation between measured LDL cholesterol levels and those calculated using the Friedewald formula, some limitations are inevitably encountered. For example, the formula cannot be employed for non-fasting samples, and is inaccurate for samples with hypertriglyceridemia (serum triglyceride levels exceeding 4.5 mmol/L)—a common finding in uremic patients—or for patients with dysbetalipoproteinemia (Nauck et al., 1996, Clin Nephrol 46: 319–325). Furthermore, this method needs measurement of three parameters to obtain LDL-C and therefore a higher variability is unavoidable. The intraclass correlation coefficients demonstrate a poor concordance between calculated and measured LDL cholesterol, both in patients and controls (Senti et al., 1996, Angiology 47: 241–246). Given the limitations of current methods and the high prevalence of CHD in North America, there is a great demand for an accurate and preferably automated method for the determination of LDL-C. Here, we propose a method based upon infrared (IR) spectroscopy for the simultaneous determination of both HDL and LDL cholesterol.

IR spectroscopy, a technique that utilizes infrared light absorption patterns to obtain structural and analytical information, has been applied previously in studies of lipoprotein structures. For instance, Scanu et al first employed IR spectroscopy to examine the thermal behavior of apoB (Scanu et al., 1969, PNAS 62: 171–178). Later on, IR was used to elucidate the secondary structure of apoIB, first qualitatively using resolution-enhancement techniques (Herzyk et al., 1987, Biochim Biophys Acta 922: 145–154) and then quantitatively using curve fitting of deconvolved spectra (Goormaghtigh et al., 1989, Biochim Biophys Acta 1006: 147–150). More recently, Goormaghtigh et al have utilized IR spectroscopy to reveal the structure of the lipid attached proteins that remain following proteolytic digestion of solvent-exposed regions (Goormaghtigh et al., 1993, Biochemistry 32: 6104–6110).

Previous studies from our group have demonstrated that a wide array of serum (Shaw et al., 1998, Ann Clin Biochem 35: 624–632) and urine (Shaw et al., 2000) analytes may be determined via IR spectroscopy of films dried from the fluid of interest. The present study reveals that the spectra of HDL and LDL cholesterol complexes are distinctive enough to permit the separate quantitation of HDL cholesterol and LDL cholesterol based upon the IR spectra of dried serum films. This finding offers a simple, reagent-free method for the simultaneous determination of HDL cholesterol, LDL cholesterol, and, as previously demonstrated (Shaw et al., 2000), total cholesterol and triglycerides.

U.S. Pat. No. 5,856,196 teaches a method of determining the level of phospholipids such as dipalmitoyl phosphatidyl choline in amniotic fluid which requires that the polar head group from the phosphoglycerides in the sample. As can be seen, this requires an added step wherein the sample must be treated prior to analysis.

U.S. Pat. No. 5,424,545 teaches a method for measuring the blood concentration of analytes such as glucose which relies on colorimetry rather than spectrophotometric means.

U.S. Pat. No. 6,026,314 teaches a noninvasive method for measuring blood component concentrations, for example, glucose or cholesterol, which comprises irradiating infrared light onto the skin of a subject.

As can be seen, the previous two patents claim methods to estimate concentrations of blood analytes such as cholesterol. However, as discussed above, cholesterol level alone is not a suitable predictor for cardiovascular health. That is, the prior art does not provide a definitive method for measuring LDL-cholesterol.

In the present study, we combined IR spectroscopy with a powerful quantitation algorithm, namely partial least squares (PLS), to assess the potential application of IR spectroscopy for the simultaneous determinations of several cardiovascular risk markers, as described below.

SUMMARY OF THE INVENTION

According to a first aspect of the invention, there is provided a method of determining the concentration of at least one cardiovascular risk marker selected from the group consisting of High Density Lipoprotein cholesterol (HDL-C), Low Density Lipoprotein cholesterol (LDL-C), and oxidized LDL comprising:

subjecting a serum sample to infra-red light;
collecting at least one spectrum of infrared light after interaction with the sample; and
determining the concentration of the cardiovascular risk marker in the sample based on the intensity of spectral features or patterns over at least one spectral range selected from the group consisting of 900–1500 $cm^{-1}$, 1500–1800 $cm^{-1}$, and 2800–3500 $cm^{-1}$.

The quantitative chemical analyses may be derived from the spectra using a quantitation algorithm, for example, partial least squares analysis.

The sample may be dried.

According to a second aspect of the invention, there is provided a method of determining the concentration of High Density Lipoprotein cholesterol (HDL-C) comprising:
subjecting a serum sample to infra-red light;
collecting at least one spectrum of infrared light after interaction with the sample; and
determining the concentration of HDL-C in the sample based on the intensity of spectral features or patterns over at least one spectral range selected from the group consisting of 900–1500 $cm^{-1}$, 1500–1800 $cm^{-1}$, and 2800–3500 $cm^{-1}$.

According to a third aspect of the invention, there is provided a method of determining the concentration of Low Density Lipoprotein cholesterol (LDL-C) comprising:
subjecting a serum sample to infra-red light;
collecting at least one spectrum of infrared light after interaction with the sample;
determining the concentration of LDL-C in the sample based upon the intensity of spectral features or patterns over at least one spectral range selected from the group consisting of 1700–1800 $cm^{-1}$, and 2800–3000 $cm^{-1}$.

According to a fourth aspect of the invention, there is provided a method of determining the concentration of oxidized LDL comprising:
subjecting a serum sample to infra-red light;
collecting at least one spectrum of infrared light after interaction with the sample;
quantifying the species of interest based upon the intensity of spectral features or patterns over at least one spectral range selected from the group consisting of 1500–1800 $cm^{-1}$, and 2800–3500 $cm^{-1}$.

BRIEF DESCRIPTION OF THE DRAWINGS

FIGS. 8A, 8B and 8C. Mid-IR spectra of native LDL and oxLDL.

FIGS. 9A and 9B. Mid-IR spectra of lipid-CH stretching vibrations.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "cardiovascular risk marker" refers to serum and/or blood analytes and includes but is by no means limited to high density lipoprotein cholesterol (HDL-C), low density lipoprotein cholesterol (LDL-C), total cholesterol, triglycerides and oxidized LDL (oxLDL).

As used herein, "serum" or "serum sample" refers to the clear liquid part of the blood that remains after blood cells and clotting proteins have been removed. Serum differs from plasma primarily in its lack of coagulation factors. It can be simply obtained by drawing blood into a test tube without anticoagulated reagents.

Described herein is a method for determining the concentration of LDL (low density lipoprotein) cholesterol, HDL (high density lipoprotein) cholesterol, total cholesterol, triglycerides and oxidized LDL from a serum sample. As will be appreciated by one knowledgeable in the art, the risk of cardiovascular disease is not simply related to cholesterol levels, but is also influenced by the ratio of LDL-C to HDL-C. In the described method, mid-infrared spectra (700–4000 $cm^{-1}$) of serum samples are acquired and quantitative information extracted using spectral features in the ranges 900–1500 $cm^{-1}$, 1700–1800 $cm^{-1}$, and 2800–3200 $cm^{-1}$. In particular, the data is analyzed as described below to determine the levels of LDL-C, HDL-C, total cholesterol, triglycerides and oxidized LDL. As discussed below, LDL levels are normally estimated using approximate methods. The present approach allows direct spectroscopic determination without resorting to such approximations. The new method would then not require fasting prior to sample submission and would be appropriate for samples with high levels of total triglycerides—two situations where the current routine analytical method fails.

Thus, the method of determining the concentration of at least one cardiovascular risk marker selected from the group consisting of High Density Lipoprotein cholesterol (HDL-C), Low Density Lipoprotein cholesterol (LDL-C), total cholesterol, triglycerides and oxidized LDL comprises: subjecting a serum sample to infra-red light; collecting at least one spectrum of infrared light from the sample; employing an appropriate quantitation algorithm, for example, partial least squares to derive quantitative information based upon spectral regions selected from the group consisting of 900–1500 cm−1, 1500–1800 cm−1, and 2800–3500 cm−1.

As discussed below, the spectrum may be analyzed using statistical analysis methods known in the art, for example, partial least squares, although other suitable methods may also be used.

EXAMPLE I

Materials

Serum specimens were collected in heparin pre-coated test tubes at the Health Science Center in Winnipeg. Standard LDL and HDL solutions were obtained from Sigma (Sigma, St. Louis, US). The experimental protocol was approved by the Human Ethics Committee of the National Research Council of Canada.

EXAMPLE II

Determination of HDL and LDL Cholesterol

The lyophilized version of the homogeneous HDL-cholesterol method from Roche Diagnostics (direct HDL-chol reagent, cat. no. 1661426; calibrator f.a.s. HDL/LDL-C, cat. no. 1778501) was used (Sugiuchi et al., 1995, Clin Chem 41: 717–723; Matsuzaki et al., 1996, J Anal Bio-Sc 19:419–427; Nauck et al., 1997, Clin Chem 43:1622–1629). In this homogeneous HDL-cholesterol method, sulfated x-cyclodextrin and dextran sulphate form, at pH 7 and in the presence of $MgCl_2$, water soluble complexes with LDL, VLDL, and chylomicrons (reagent 1), which are not accessible to PEG-coupled cholesterol esterase and cholesterol oxidase (reagent 2). The HDL-cholesterol fraction is then directly estimated by the fully automated analyzer application.

LDL-cholesterol (LDL-C) was calculated using the formula developed by Friedewald et al. (Friedewald et al, 1972) for subjects with triglycerides <4.0 g/L (<400 mg/dL. LDL-C values were not available for those subjects with triglycerides levels above this threshold).

EXAMPLE III

Infrared Spectra

A total of 5 µl of the serum was evenly spread on an infrared transparent calcium fluoride window (13 mm diameter) and allowed to dry under a light vacuum (25 Torr) to produce a glassy film. A blank calcium fluoride window was used as background. A home-made multi-sampler wheel was used which allows measurement of 14 separate spectra in a single run without repeatedly measuring the background. In other embodiments, a blank calcium fluoride window was used for the background measurement. Infrared spectra of such films were recorded with a Bio-Rad FTS-40AIR spectrometer (Bio-Rad Laboratories, Cambridge, Mass.) at a nominal resolution of 2 $cm^{-1}$. Measurement time was 5 minutes (256 scans signal averaged) for each film. For each subject sample we measured spectra for two separate films.

EXAMPLE IV

Regression Analysis

The infrared spectrum of serum includes spectral contributions from protein, cholesterol, triglycerides, urea, glucose, and other more dilute compounds. Because each individual component contributes a complex set of several absorptions falling throughout the mid-IR range, it is impossible to find any single absorption band that can serve as the basis to quantitate any single component; coincident absorptions from other species would degrade or completely sabotage the effort. For that reason, IR-based analytical methods are very commonly based upon methods such as partial least squares (PLS), that utilize spectral information spread across a wider spectral range (Shaw et al., 1998, Ann. Clin. Biochem. 35: 624–632; Martens H, Næs T. Multivariate Calibration. New York: John Wiley and Sons, 1989; Beebe and Kowalski, 1987, Anal. Chem. 59:1007a–17a.). Within this approach, infrared spectroscopy is a secondary analytical method. The IR-based analytical method is derived by first acquiring a set of specimens that I) encompasses the full range of concentrations expected in routine assays for the analyte of interest, and II) include any interferents that might appear in the course of routine analysis. Infrared spectra are then acquired for these specimens, which are analyzed in parallel for the analyte(s) of interest using standard methods, and the PLS technique is then employed to derive an algorithm relating the spectra to corresponding analyte concentrations.

In essence, the process is to reconstruct all spectra from a limited set of artificial spectra (PLS 'factors')—a procedure that in turn provides an algorithm to convert spectra to concentrations for the analyte of interest. From a practical perspective, the procedure uses any of several widely available software packages that take as input the spectra and corresponding analyte concentrations, and provide the quantitation algorithm, termed the 'PLS calibration model' as output. These packages offer the user the flexibility to explore various options, for example preprocessing the spectra (e.g. normalization and derivation), selecting restricted spectral ranges (PLS typically works most effectively if spectral regions containing no signal from the analyte of interest are omitted), and seeking the optimal number of factors to include in the calibration model.

The PLS approach was used for the quantitation of LDL-C, HDL-C, total cholesterol, and triglycerides from the infrared spectra of these serum samples. Quantitation models derived on the basis of the training set were gauged by their accuracy in predicting the analyte levels for an independent set of test specimens (about ⅓ of the total specimens, i.e. those samples that were not included in the training set). PLS calibrations and spectral manipulations were carried out using GRAMS/32 software packages (Galactic Industries, Salem, N.H. 03079). In each case the first step was to identify a set of spectra (60 specimens, 120 spectra) to serve as the basis for PLS model calibration. A PLS calibration model was then developed and validated by using it to predict the analyte levels for to predict analyte levels for the remaining 30 samples (60 spectra) on the basis of their IR spectra.

EXAMPLE V

Results

Infrared Spectra of HDL and LDL

Lipoproteins are spherical particles whose central core is occupied by non-polar lipids (e.g. cholesterol esters and triglycerides), with more polar lipids such as free cholesterol and phospholipids on the periphery. Six major classes have been specified, namely chylomicrons, VLDL (very low density lipoproteins), IDL (intermediate density lipoproteins), LDL, HDL, and lipoprotein(a) (Lp(a)). The series ranging from chylomicrons through HDL are ordered in increasing density, from <0.95 to 1.21 g/mL, and decreasing lipid:protein ratio, from 99:1 (chylomicrons) to 50:50 (HDL). The IR spectra of LDL and HDL would be expected to reflect differences in lipid:protein ratio (80:20 for LDL vs. 50:50 for HDL. The two fractions are also distinguished by the nature of the lipid constituents—primarily cholesterol esters for LDL and phospholipids for HDL—as well as by the differences in the constituent proteins (ApoB 100 for LDL; ApoA-I and ApoA-II for HDL). To characterize the corresponding IR spectral differences, the infrared spectra of LDL, HDL are reported in FIG. 1 together with a representative spectrum of a dry serum film.

Figure 1:
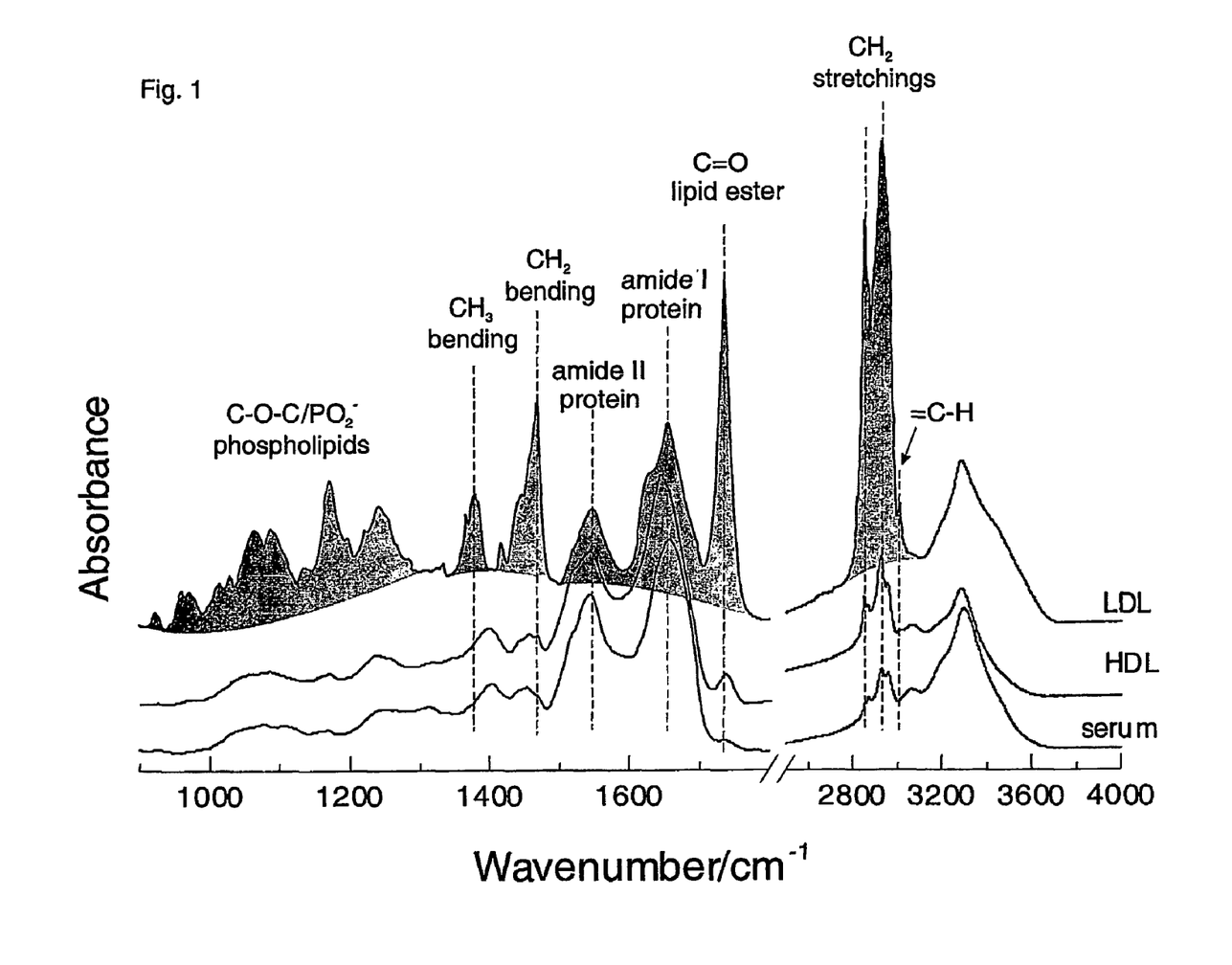
FIG. 1. Comparison of the mid-infrared (mid-IR) spectra of dry LDL, HDL and serum specimens.

From the infrared spectra, one can readily gather general information concerning the molecular constituents and their structures. For instance, there are two prominent amide absorptions, one at approximately 1655 $cm^{-1}$, (arising from C=O stretching, and termed the amide I band) and another at approximately 1546 $cm^{-1}$, originating from N—H bending (termed the amide II band) vibrations of the peptide groups in proteins. The sharp absorption at 1467 $cm^{-1}$ is attributed to the bending (scissoring) vibrations of the $CH_2$ groups of the lipid acyl chains, with the shoulder at 1446 $cm^{-1}$ arising from the asymmetric bending vibration of the $CH_3$ groups of both lipid and protein constituents. The $CH_3$ symmetric bending vibration gives rise to the absorption at 1378 $cm^{-1}$. Absorptions at approximately 1242 and 1088 $cm^{-1}$ come from the $PO_2^-$ asymmetric and symmetric stretching vibrations of the phosphodiester groups of phospholipids. The remaining absorptions originate from ester C-0-C asymmetric and symmetric stretching vibrations (approximately 1173 and 1065 $cm^{-1}$ respectively) of phospholipids, triglycerides and cholesteryl esters. The most prominent lipid absorption is that in the LDL spectrum at approximately 1736 $cm^{-1}$, arising predominantly from the ester C=O groups of cholesterol esters, while the strong bands at approximately 2852 and 2926 $cm^{-1}$ originate with the symmetric and asymmetric stretching vibrations of the lipid acyl $CH_2$ groups. While a number of additional absorptions appear, it is the lipid absorptions that give rise to most dramatic differences among the spectra, with the spectrum of LDL standing out in particular as a consequence of its high lipid content.

Figure 2:
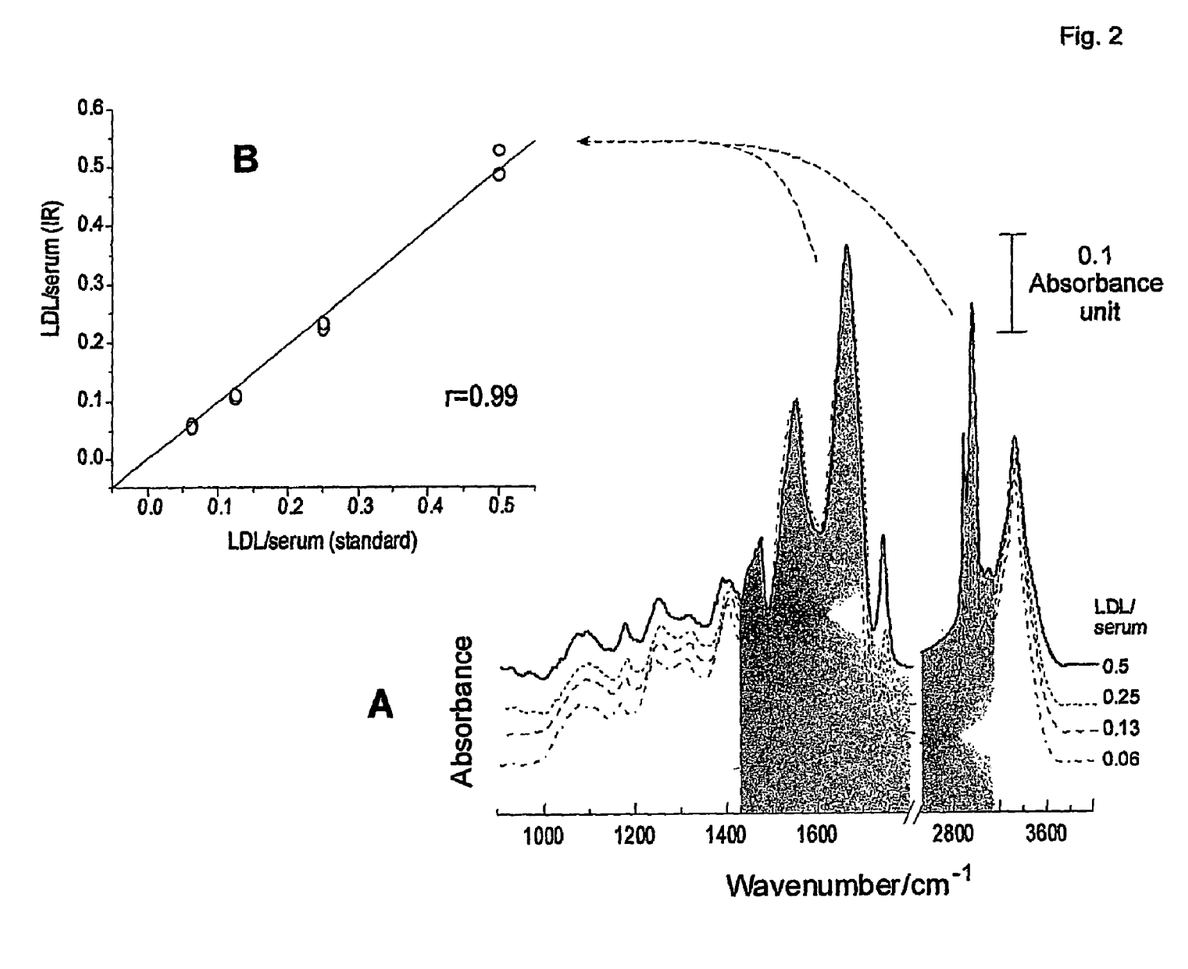
FIG. 2. Mid-IR spectra for a series of dried LDL/serum mixture (A). The inset shows the correlation between band intensity in the shaded area and the composition of LDL/serum mixtures (B).
Figure 3:
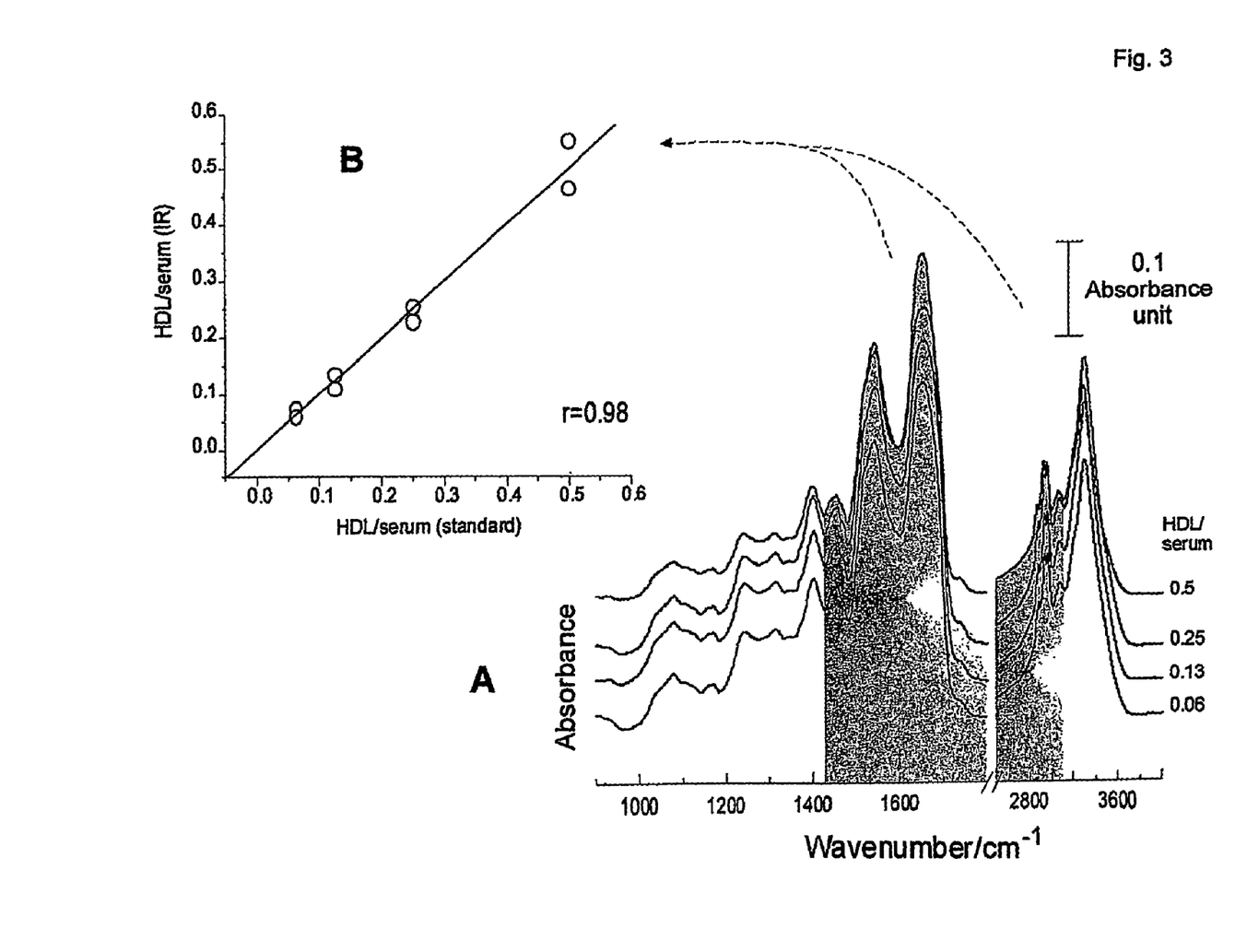
FIG. 3. Mid-IR spectra for a series of HDL/serum mixtures (A). The inset shows the correlation between band intensity in the shaded area and the composition of HDL/serum mixtures (B).

The fact that the spectra of LDL and HDL are clearly different from one another supports the notion that HDL and LDL can be quantified separately, based upon IR spectroscopy of serum. Next, a series of experiments were carried out to establish whether the absorbance intensity of LDL (or HDL) preparations added to serum is proportional to LDL (or HDL) concentration in serum. For this purpose, the spectral regions 1450–1800 and 2800–3200 $cm^{-1}$ were chosen since these regions encompass the major absorptions of the lipid and protein constituents. The first LDL serum mixture was 50:50 LDL:serum, with additional solutions prepared by further 50:50 dilutions of this mixture with the original serum specimen. FIG. 2A shows the spectra for four of these LDL/serum mixtures. As expected, the intensities in the three major lipid bands (approximately 1736, 2852 and 2926 $cm^{-1}$) gradually decreased with dilution of the LDL-solution. More subtle changes are also observed for the protein amide bands, with both the band position and relative intensities altered with the gradual dilution of LDL in serum. Most importantly, there is a good correlation between the integrated absorbance (band area) and the LDL cholesterol concentration in the mixture (FIG. 2B). The same experiment was carried out in HDL and serum mixtures, and the spectra of four mixtures are shown in FIG. 3A. While the naked eye reveals few clear differences among these spectra, the integrated intensity within the shaded band areas (1450–1800. and 2800–3200 $cm^{-1}$) shows a good correlation with HDL cholesterol concentration (FIG. 3B).

These experiments confirm that HDL and LDL have characteristic absorption bands, and that the absorbance intensity can be related to the analyte concentration through the Beer-Lambert relationship (Liu and Mantsch, 1999, Am J Obstet Gynecol 180: 696–702). These findings provide a sound basis to expect that both LDL and HDL cholesterol may be quantitated based upon the IR spectrum of serum, as summarized in the following section.

Quantitation of LDL-C, HDL-C, Cholesterol, and Triglycerides

Figure 4:
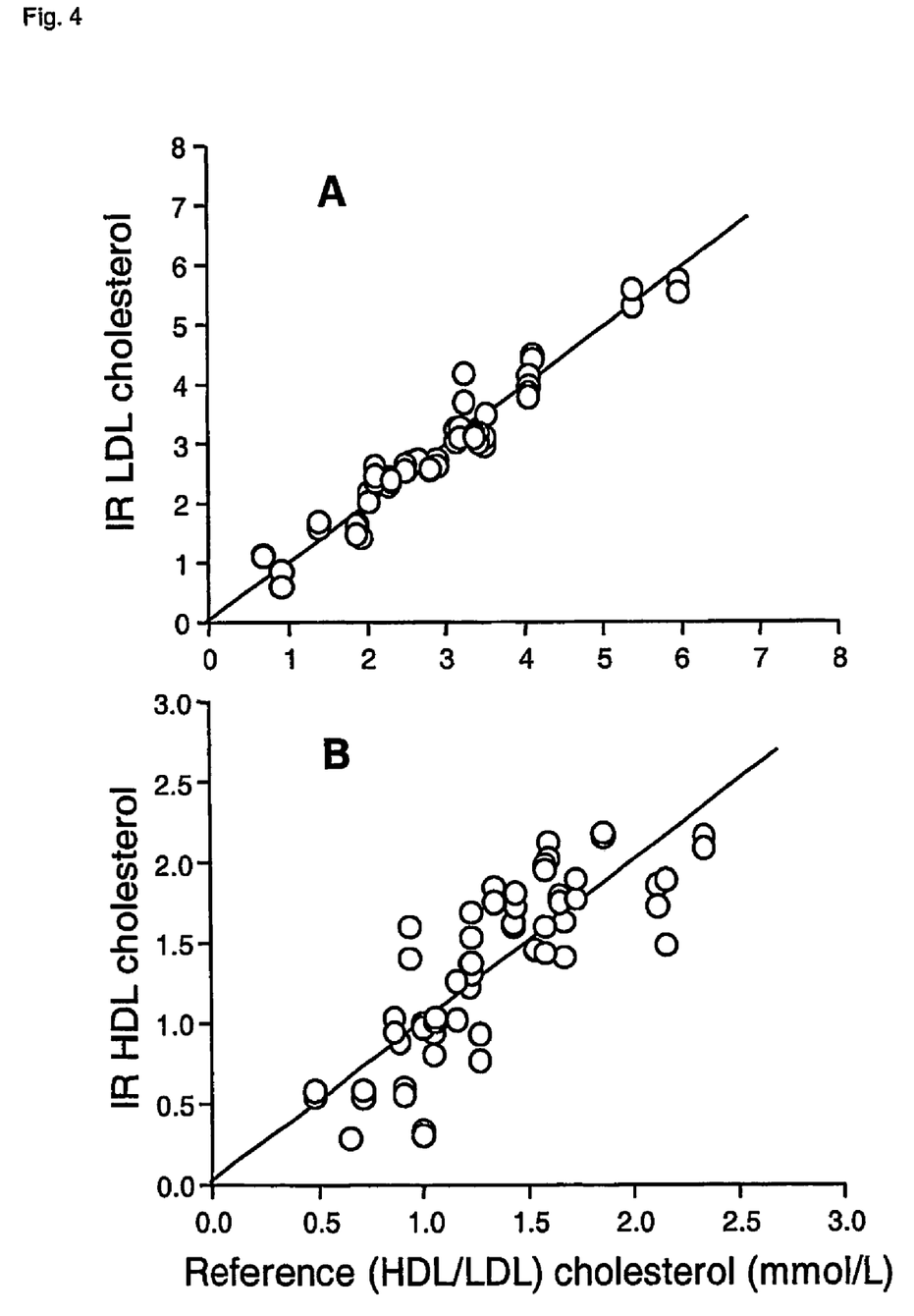
FIGS. 4A and 4B. Comparison of mid-IR-derived HDL and LDL cholesterol levels with values provided by accepted clinical laboratory methods. The line of identity is included for reference. Best-fitting regression lines y=Ax+B are for LDL cholesterol A=0.90, B=0.30, r=0.96, and for HDL cholesterol A=1.0, B=0.01 r=0.82.
Figure 5:
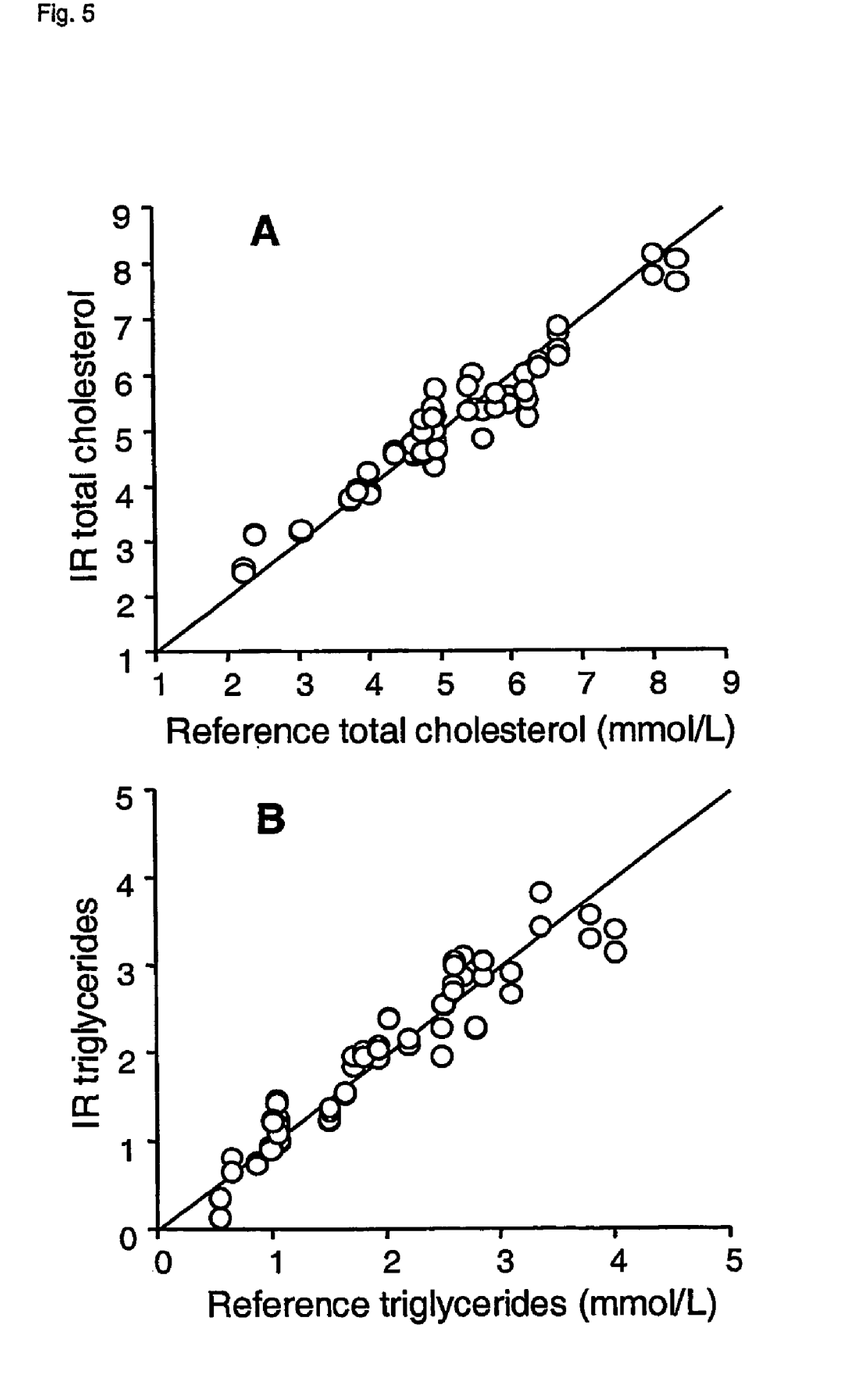
FIGS. 5A and 5B. Comparison of IR-derived total cholesterol and triglycerides levels with values provided by accepted clinical laboratory methods. The line of identity is included for reference. Best-fitting regression lines y=Ax+B are for total cholesterol A=0.85, B=0.30, r=0.93, and for triglycerides A=0.91, B=0.17, r=0.95.

A training set of 120 spectra was used to build each of the four PLS calibration models, while the test set was made up of 60 different spectra. FIG. 4 compares the mid-IR-predicted HDL and LDL cholesterol levels to the clinical laboratory results for the test samples. Details of the PLS models are summarized in Table 1 while the scatterplots for cholesterol and triglycerides are shown in FIG. 5.

Near-IR Spectral Analysis

A total of 207 near-infrared spectra were obtained from 207 serum samples using. Near-IR spectra were recorded in the range of 400–2500 nm on a NIRSystems spectrometer (Model 6500, Silver Springs, Md.), using a 10 nm bandpass and 2 nm between data points. For measurement, serum aliquots (about 350 µl) were placed in an optical glass cell with a pathlength of 0.5 mm and 64 scans were coadded over a measurement time of about 60 seconds. This single beam was then ratioed against a reference single beam spectrum (no sample in place) and converted to absorbance units.

Figure 6:
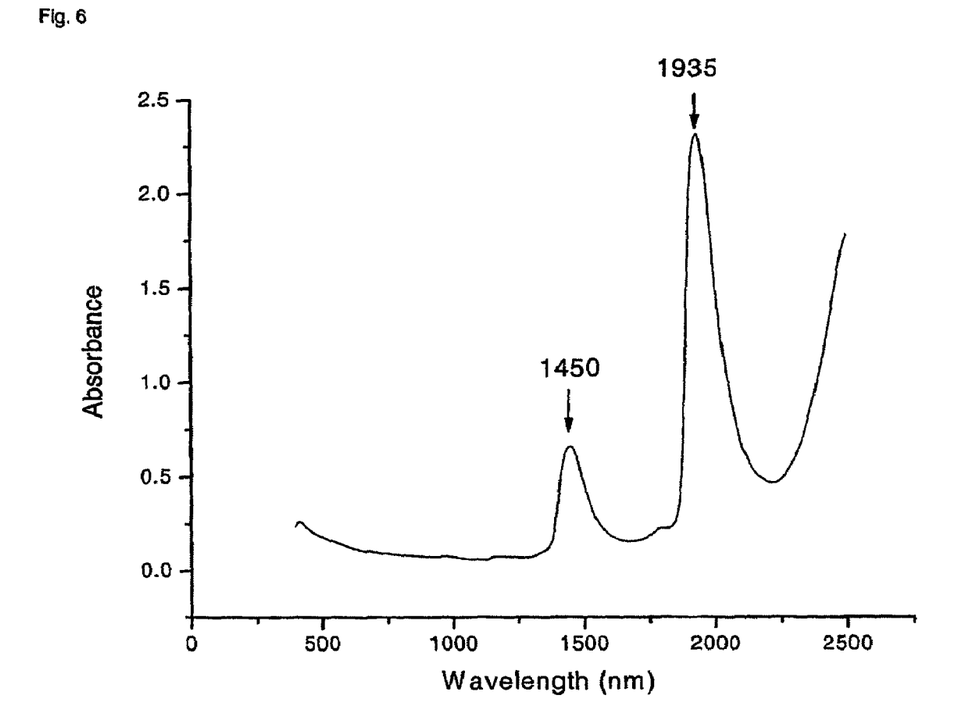
FIG. 6. Near-infrared (near-IR) spectrum of serum.

A representative near-IR spectrum of serum is shown in FIG. 6. The main characteristics of this spectrum are two strong absorption bands centered at approximately 1450 and 1935 nm, which arise from water and dominate the spectra of all biological fluids. Specific absorptions that originate from organic serum components are most prominent in the region 2000 to 2500 nm and arise from stretching vibrations of X—H groups (where X is O, N or C). While many of these absorption bands are superficially weak, they contribute significantly to the characteristic band profile in the 2000–2500 nm region and can be used for quantitative analysis.

Quantitative analysis was achieved by relating the observed spectral features to the concentrations of the analytes present in the sample. The concentration of an analyte, C, is related to its spectral intensity at wavelength $\lambda_1$, $A(\lambda_1)$, through Beer's law as:

$$C = K_0 + K \cdot A(\lambda_1)$$

where $K_0$ and $K_1$ are the intercept and slope, respectively. Extensions to this fundamental relationship have been conceived, for example, partial least square analysis (PLS), to correlate the variations in spectral intensity with the concentration of the analyte under investigation. The procedure, which is based fundamentally on the concentration/absorbance relationship shown above, involves the generation of a set of factors from the measured spectra and the known analyte concentrations. A linear combination of these factors (calibration equation) is then used to correlate the spectral variations with the analyte concentration in the spectra. The salient features of the PLS technique are summarized above. Second derivative spectra were evaluated to enhance the generally weaker but narrower solute absorption bands of interest. The derivative spectra (2000–2460 nm range) and the reference LDL cholesterol concentration were subjected to PLS analysis, which produced a calibration equation that was then used to predict the LDL cholesterol concentration for the same samples.

Figure 7:
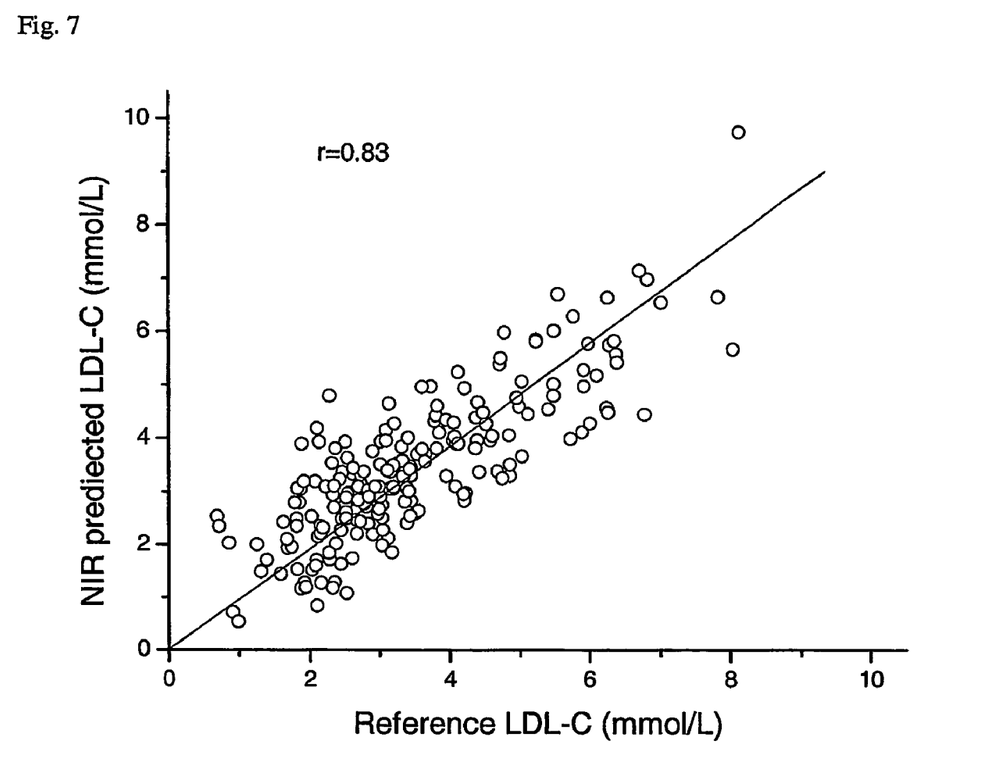
FIG. 7. Scatterplot comparing near-IR-predicted LDL-C concentrations to those obtained using standard techniques.

FIG. 7 shows a scatterplot comparing the LDL cholesterol concentrations predicted from the near-IR spectra to those provided by the standard (Friedewald) clinical chemistry analytical method. The two methods are in close agreement (r=0.83 and standard deviation 0.84), indicating that the near-IR approach can be used for the quantitation of serum LDL.

Oxidized LDL

For several years it has been known that development of atherosclerosis is related to the level of the "noxious" low density lipoproteins (LDL). More recent studies have revealed that the ultimate atherogenic agents are in fact modified, mainly oxidized, forms of LDL. Oxidative damage to LDL may range from slight structural alterations (mildly oxidized LDL) to extensive breakdown of lipids and apolipoprotein B (fully oxidized LDL). In vitro studies as well as studies with experimental animals show that the various oxidized forms of LDL contribute to atherogenic processes by multiple mechanisms.

Despite convincing evidence from in vitro and animal studies, knowledge regarding the role of oxidized LDL in the development of atherosclerosis in humans remains limited. One reason for the paucity of human studies has been that there is no good routine method for the direct measurement of oxidized LDL, hence no large-scale epidemiologic studies. To date, in vivo LDL oxidation has been estimated by determination of autoantibodies to oxidized LDL. This methodology, however, is not practical for routine clinical purposes. In particular, reproducible preparation of antigens (oxidized LDL) is impossible in practice. This has led to imprecision in the measurements, most notably between laboratories, and direct comparison of results from different laboratories is therefore not recommended. Thus, there is need for a rapid and specific measure of LDL oxidation for the diagnosis and management of atherosclerosis. To that end, mid-IR spectroscopy (IR), was evaluated for its ability to I) detect qualitatively whether LDL is oxidized and II) if so, whether mid-IR spectroscopy can provide a basis to determine the concentration of oxidized LDL quantitatively in serum.

Figure 8:
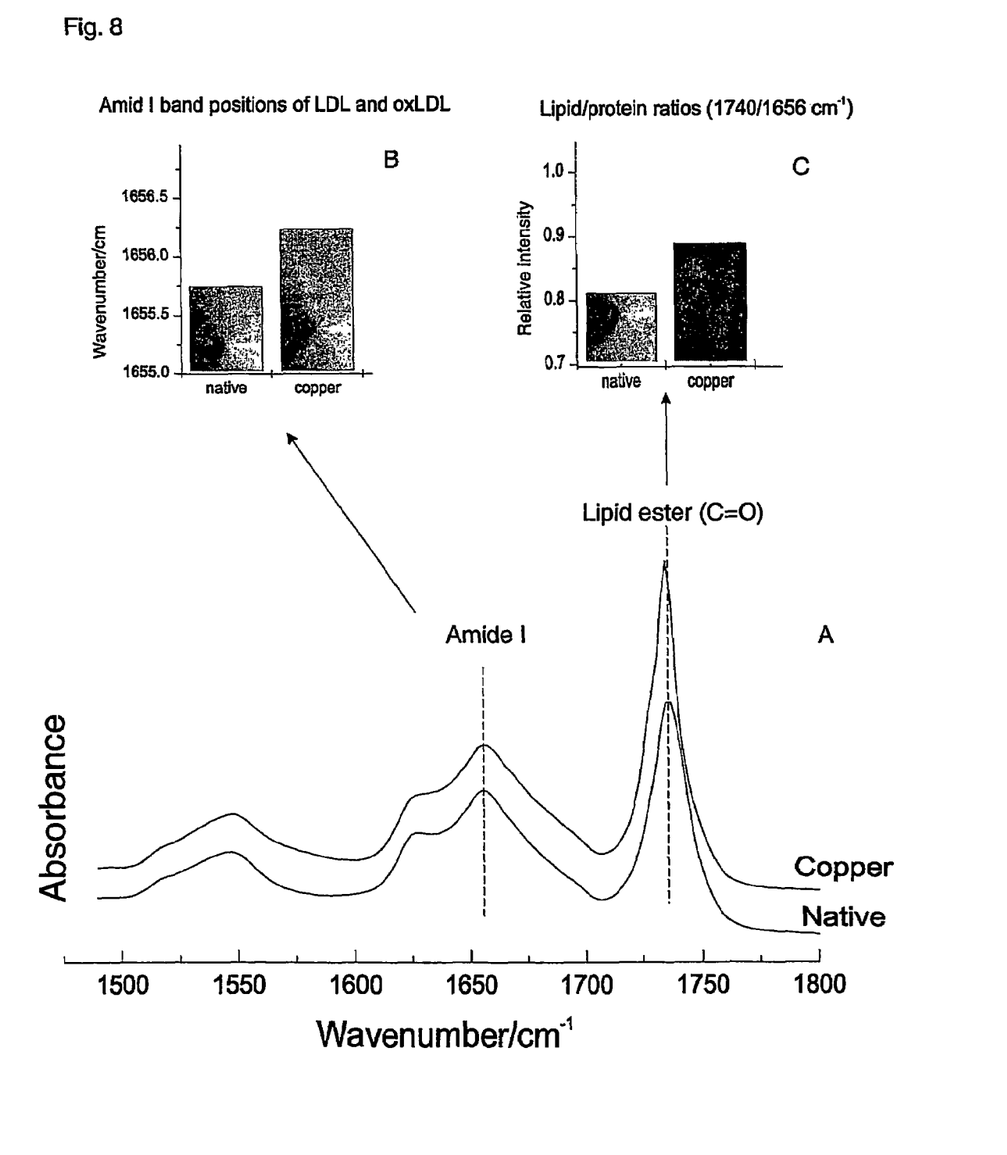
FIG. 8A displays the spectra in the spectral range 1500–1800 $cm^{-1}$ of native LDL and oxidized LDL (oxLDL) derived from the incubation of 5 μM $CuSO_4$ for 24 hours.
FIG. 8B shows amide I band positions of LDL and oxoLDL.
FIG. 8C shows the ratio of intensities for lipid and protein absorptions at approximately 1740 $cm^{-1}$ and 1656 $cm^{-1}$ respectively.

FIG. 8 displays the spectra in the spectral range 1500–1800 $cm^{-1}$ of native LDL and oxidized LDL (oxLDL) derived from the incubation of 5 μM $CuSO_4$ for 24 hours. Several qualitative changes can be observed upon oxidation. First, the major amide I absorption (arising mainly from C=O stretching vibration in the protein backbone) is shifted for oxLDL as compared to native LDL. As demonstrated in FIG. 8B, the amide I band is shifted to higher frequency for oxLDL, consistent with a change in the structure of Apo B-100, the major Apo protein constituent of oxLDL. Second, the lipid ester band (C=O) located at approximately 1740 cm-1 in the oxLDL has greater intensity that the corresponding absorption for native LDL (FIG. 8A). By evaluating the ratio of intensities for lipid and protein absorptions at approximately 1740 and 1656 $cm^{-1}$ respectively, we can clearly distinguish oxidized form native LDL (FIG. 8C). It is clear that the relative lipid content in the oxLDL has increased, consistent with the esterification of lipids in oxLDL.

Figure 9:
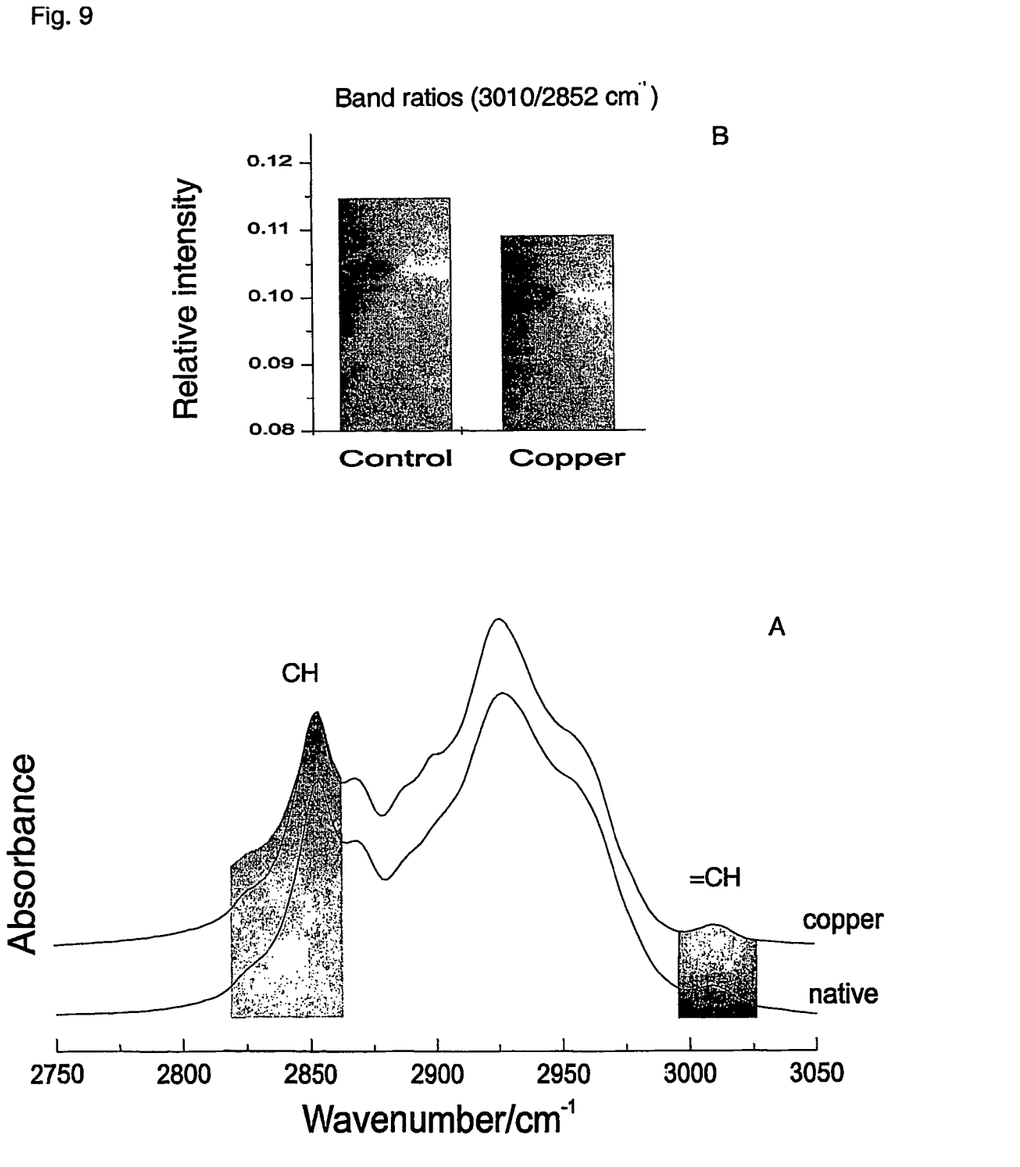
FIG. 9A displays the spectra in the spectral range 2750–3050 $cm^{-1}$ of native LDL and oxidized LOL (oxLDL) derived from the incubation of 5 μM $CuSO_4$ for 24 hours.
FIG. 9B shows the ratio of intensities for =CH and $_{sy}CH_2$ absorptions at approximately 3010 $cm^{-1}$ and 2851 $cm^{-1}$ respectively.

We have further explored the spectral range between 2800–3050 $cm^{-1}$, where IR bands arise from lipid CH stretching vibrations (FIG. 9). The band at approximately 2851 $cm^{-1}$ ($_{sy}CH_2$) corresponds to the symmetric stretching vibration of the acyl chain $CH_2$ groups whereas the approximately 3010 $cm^{-1}$ originates from the CH vibrations of =CH double bonds within unsaturated fatty acyl esters (e.g. linolenic, arachidonic, etc.) or cholesterol in LDL. The ratio of integrated area (—CH/$_{sy}CH_2$) therefore provides a spectroscopic index of the relative concentrations of native to oxidized LDL. FIG. 9B shows that the ratio of =CH/$_{sy}CH_2$ in the oxidized LDL is decreased compared to that found in native LDL.

These data confirm that there are qualitative alterations in the IR spectrum of oxLDL as compared to native LDL, and therefore that IR spectroscopy provides the basis for a quantitative assay of oxidized serum LDL.

EXAMPLE VI

Discussion

Cardiovascular disease remains the leading cause for the mortality in North America, and LDL is the major lipoprotein fraction responsible for the development of atherosclerotic lesions. Assessment of the risk of coronary heart disease requires measurement of both HDL-C and LDL-C levels. We have explored here the possibility that IR spectroscopy might provide the means to simultaneously measure both LDL and HDL cholesterol concentrations in the serum. The results indicate that IR spectroscopy can provide a simple and rapid means to recover both serum HDL and LDL cholesterol levels, and that another risk factor, oxidized LDL, may also be quantified based upon the infrared spectrum of serum The approach is particularly attractive in that the same serum spectrum also yields both total cholesterol and triglyceride levels.

Previous IR studies of LDL and HDL have been aimed at the elucidation of the protein secondary structure (for a review see Surewicz et al., 1993, Biochemistry 32: 389–394). For example, the secondary structure of the protein present in human LDL, namely apo B-100, has been investigated by transmission and attenuated total reflection infrared spectroscopy. The amount of β-sheet (41%) was significantly higher than that determined by CD spectroscopy both in the same study (12%) and elsewhere (15–16%). The high percentage of β-sheet structure in apo B-100 was suggested to substantiate the importance of such segments in maintaining the lipid-protein assembly in LDL (Goormaghtigh et al, 1989). A more recent study reported the secondary structure at 37° C. to be 24% α-helix, 23% β-sheet, 6% β-turns, 24% unordered structure, and 24% "β-strands," characterized by a band around 1618 $cm^{-1}$, and consistent with extended string-like chains in contact with the lipid moiety not forming β-sheets (Banuelos et al., 1995, JBC 270: 9192–9196).

The IR-based analytical method has certain fundamental advantages over the current status quo for LDL measurement in particular. The current state of the art is to estimate LDL cholesterol concentrations by using the Friedewald formula. This approach derives the LDL-C from total cholesterol, HDL-C, and VLDL-C (very low density lipoprotein cholesterol) concentrations as follows:

[LDL-C]=[total cholesterol]−([HDL-C]+[VLDL-C])

where the VLDL-C concentration is estimated from the serum triglyceride concentration (in mmol/L) as [VLDL-C]=[triglycerides]/2.22 (Friedewald et al, 1972). This relationship assumes the ratio of total triglycerides to VLDL cholesterol (VLDL-C) to be constant in all samples. However, there are some limitations to this approximation. For instance, the formula will overestimate VLDL-C—and underestimate LDL-C as a consequence—if triglyceride-rich chylomicrons and chylomicron remnants are present in the serum specimen (hence the requirement for a fasting sample) (Cohn et al., 1988, Clin Chem 34: 2456–2459). In addition, the ratio of total triglycerides to VLDL-C changes with increasing triglyceride levels. Therefore, it has been recommended that the Friedewald formula not be applied in sera with total triglycerides above 4.56 mmol/L (400 mg/dL). The use of the Friedewald formula is also not recommended for type II diabetes patients, since accompanying abnormalities in lipoprotein composition render the underlying assumptions invalid for assessment of cardiovascular risk in these patients (Rubies-Prat et al., 1993, Diabetes Care 16: 1081–1086). For the same reason, the Friedewald formula may be inappropriate in chronic alcoholics, particularly those in whom a degree of hepatic dysfunction may be suspected (Matas et al., 1994, Clin Chem 40:404–406).

One reason that the Friedwald formula survives despite its known deficiencies is that it closely mimics the analytical method originally used to develop LDL-C reference intervals. A second, more pragmatic reason is that there are no convenient alternatives to the Friedewald formula. There are a number of methods that are more soundly based. The most obvious example is the first, so-called beta quantification method. A combined ultracentrifugation polyanion precipitation method that involves the preparation and cholesterol analysis of appropriate lipoprotein fractions. However this approach is far too time consuming and expensive for routine use. Another example is preparative ultracentrifugation and lipoprotein electrophoresis followed by either polyanion detection or enzymatic staining of cholesterol (Weiland and Seidel, 1973, Clin Chem 19: 1139–1141; Nauck et al., 1995, Clin Chem 41: 731–738). Again, these approaches are too cumbersome for routine screening use.

As discussed above, the IR-based LDL method surmounts the deficiencies inherent to the Friedewald equation. As the method is based upon IR spectroscopic features that uniquely characterize the LDL-C serum component, it provides for accurate analyses even for those samples that are inappropriate for use of the Friedewald approximation. Thus, the IR-based method would also distinguish LDL-C from IDL-C and Lp(a) lipoprotein fractions that are normally pooled together with true LDL-C and assumed to be negligible by comparison.

While the preferred embodiments of the invention have been described above, it will be recognized and understood that various modifications may be made therein, and the appended claims are intended to cover all such modifications which may fall within the spirit and scope of the invention.

TABLE 1

Summary of PLS models

| Analytes | Spectral Region(s) (cm$^{-1}$)[a] | # of factors[b] | $S_{y/x}$(mmol/L) |
|---|---|---|---|
| HDL cholesterol | 900–1500, 1700–1800, 2800–3500 | 6 | 0.31 |
| LDL cholesterol | 1700–1800, 2800–3000 | 8 | 0.35 |
| Total cholesterol | 1700–1800, 2800–3000 | 10 | 0.38 |
| Triglycerides | 2800–3200 | 7 | 0.35 |

[a]Spectral regions employed for the PLS models
[b]Number of factors included in the optimal PLS models

What is claimed is:

1. A method of determining the concentration of High Density Lipoprotein cholesterol (HDL-C) comprising:
   subjecting a serum sample to infra-red light;
   collecting at least one spectrum of infrared light after interaction with the sample; and
   determining the concentration of HDL-C in the sample based on the intensity of spectral features or patterns over at least one spectral range selected from the group consisting of 900–1500 cm−1, 1500–1800 cm−1, and 2800–3500 cm−1.

2. The method according to claim 1 wherein the concentration of HDL-C is derived from the spectra using a quantitation algorithm.

3. The method according to claim 2 wherein the quantitation algorithm is partial least squares analysis.

4. A method of determining the concentration of Low Density Lipoprotein cholesterol (LDL-C) comprising:
   subjecting a serum sample to infra-red light;
   collecting at least one spectrum of infrared light after interaction with the sample;
   determining the concentration of LDL-C in the sample based upon the intensity of spectral features or patterns over at least one spectral range selected from the group consisting of 1700–1800 cm−1, and 2800–3000 cm−1.

5. The method according to claim 4 wherein the concentration of LDL-C is derived from the spectra using a quantitation algorithm.

6. The method according to claim 5 wherein the quantitation algorithm is partial least squares analysis.

* * * * *